United States Patent [19]
Ogata et al.

[11] Patent Number: 5,674,528
[45] Date of Patent: Oct. 7, 1997

[54] HEMOGLOBIN-ENCAPSULATED LIPOSOME

[75] Inventors: Yoshitaka Ogata; Takeshi Okamoto, both of Kanagawa, Japan

[73] Assignee: Terumo Kabushiki Kaisha, Tokyo, Japan

[21] Appl. No.: 490,509

[22] Filed: Jun. 14, 1995

[30] Foreign Application Priority Data

Jun. 15, 1994 [JP] Japan .................................. 6-133043
Jun. 15, 1994 [JP] Japan .................................. 6-133052

[51] Int. Cl.$^6$ .................................................. A61K 9/127
[52] U.S. Cl. ........................... 424/450; 264/4.1; 264/4.6
[58] Field of Search ..................... 424/452; 428/402.2; 264/4.1, 4.6

[56] References Cited

U.S. PATENT DOCUMENTS

| | | | |
|---|---|---|---|
| 4,133,874 | 1/1979 | Miller | 424/38 |
| 4,321,259 | 3/1982 | Nicolau et al. | 424/101 |
| 4,376,059 | 3/1983 | Davis et al. | 252/316 |
| 4,439,357 | 3/1984 | Bonhard et al. | 260/112 B |
| 5,039,665 | 8/1991 | Markov | 514/23 |

FOREIGN PATENT DOCUMENTS

| | | |
|---|---|---|
| 0158684 | 10/1985 | European Pat. Off. |
| 0170247 | 2/1986 | European Pat. Off. |
| 0395382 | 10/1990 | European Pat. Off. |
| 2-178233 | 7/1990 | Japan |
| 4-59735 | 2/1992 | Japan |
| 87/05300 | 9/1987 | WIPO |

OTHER PUBLICATIONS

Beissinger et al, Liposome-encapsulated Hemoglobin as a Red Cell Surrogate—Preparation Scale-up, Jul.–Sep. 1986, 58–63.

Abstract, AN 89-117245, Derwent Publications Ltd., London, Mar. 8, 1989.

Abstract, AN 87-259765, Derwent Publications Ltd., London, Aug. 5, 1987.

Okamoto Takeshi, Liposome Containing Hemoglobin and Preparation Thereof, Jul. 11, 1990, Patent Abstracts of Japan—JP-A-02 178 233.

Abstract, AN 92-118330, Derwent Publications Ltd., London, Feb. 26, 1992.

Abstract, AN 75-68422W, Derwent Publications Ltd., London, Mar. 24, 1975.

Szebeni et al, *Biochemistry*, "Encapsulation of Hemoglobin in Phospholipid Liposomes: Characterization and Stability", vol. 24, (1985), pp. 2827–2832.

*Primary Examiner*—Gollamudi S. Kishore
*Attorney, Agent, or Firm*—Burns, Doane, Swecker & Mathis, LLP

[57] ABSTRACT

A hemoglobin-encapsulated liposome is provided. The hemoglobin-encapsulated liposome comprises a liposome and an enzymatically active hemoglobin solution encapsulated therein. The hemoglobin solution is supplemented with glucose; and at least one member selected from the group consisting of adenine, inosine, and adenosine triphosphate; and optionally, further with phosphoenol pyruvate. The thus supplemented hemoglobin solution encapsulated in the liposome exhibits an improved resistance to conversion to methemoglobin as well as an adequately regulated affinity for oxygen. Therefore, the hemoglobin-encapsulated liposome of the present invention is useful as a blood substitute.

12 Claims, 6 Drawing Sheets

HEMOGLOBIN-ENCAPSULATED LIPOSOME

BACKGROUND OF THE INVENTION

This invention relates to a hemoglobin-encapsulated liposome adapted for administration to a body. More particularly, this invention relates to a hemoglobin-encapsulated liposome wherein in vivo oxidation of the encapsulated hemoglobin into methemoglobin after the administration is minimized. This invention also relates to a hemoglobin-encapsulated liposome wherein the hemoglobin would exhibit an appropriately regulated affinity for oxygen.

Typical blood substitutes that are currently in use include plasma expanders such as gelatin lysate solutions, dextran solutions, and hydroxyethyl starch (HES) solutions. Such blood substitutes, however, are preparations that have been developed in order to make up for the plasma in blood vessels and maintain blood circulation dynamics upon large-volume hemorrhage and other emergency occasions. Accordingly, such blood substitutes were incapable of substituting the oxygen-transportation capacity of the natural erythrocytes. Apart from such plasma expanders, development of artificial oxygen carriers is on its way for use as blood substitutes provided with the oxygen-transportation capacity analogous to that of the natural erythrocytes.

At the initial stage of such development, chemically synthesized products utilizing the high oxygen-dissolving capacity of a fluorocarbon emulsion (perfluorochemical, PFC, often referred to as fluorocarbon) that is as high as 20 times that of water were investigated. Such chemically synthesized products, however, were still insufficient in the oxygen transportation capacity, and moreover, suffered from the risk of accumulation in the body.

In the meanwhile, attempts have been made to utilize hemoglobin from natural erythrocytes for the oxygen carrier. Use of free hemoglobin, however, has proved difficult since free hemoglobin suffers from an extremely short half time of not more than 4 hours in the body. Free hemoglobin also suffers from low oxygen-transportation capacity to periphery and toxicity to kidney. Consequently, interests in the development have shifted to modified hemoglobins (stabilized hemoglobins, polymerized hemoglobins, etc.) and liposome encapsulated hemoglobin incorporated in liposomes, wherein the problems associated with the free hemoglobin have been obviated.

A typical hemoglobin-encapsulated liposome produced by thin film process is reported by Miller (U.S. Pat. No. 4,133,874). In this process, the hemoglobin-encapsulated liposomes are produced by dissolving a liposome-forming lipid in an adequate organic solvent such as chloroform, distilling off the organic solvent from the resulting solution to form a thin film of the lipid, adding the hemoglobin solution obtained by hemolysis onto the thus formed thin film, vigorously agitating the solution to form multilayer liposomes, and ultrasonically treating the thus formed multilayer liposomes.

It is the reversible bonding of the oxygen molecule to the hemoglobin that is responsible for the oxygen-transportation capacity of the artificial erythrocytes prepared from the hemoglobin, and the oxygen-transportation capacity is a function that is present only under the conditions that the iron in the hem (protohem) is in its divalent state (i.e. $Fe^{2+}$). Hemoglobin gradually becomes oxidized in its course of repeated reversible oxygenation, and methemoglogin wherein the iron is in its trivalent state ($Fe^{3+}$) is produced. Methemoglobin has no oxygen-bonding capacity. Normal erythrocyte in blood has a mechanism capable of suppressing such hemoglobin oxidation. The hemoglobin solution prepared as an artificial oxygen carrier, however, lacks such oxidation suppression mechanism as found in natural erythrocytes. Consequently, the proportion of the oxidized hemoglobin increases with lapse of time. In view of such situation, it has been necessary, upon use of the natural hemoglobin or its derivative for a medical product or reagent, to add an antioxidant or a reducing agent such as sodium sulfite, sodium hydrogensulfite, ferrous sulfate, or sodium ethylenediaminetetraacetate, that is toxic for the organism. It has also been commonplace to add reduced-form glutathione, ascorbic acid, a tocopherol, a sugar, an amino acid, or the like. These additives, however, have proved insufficient in suppressing the hemoglobin oxidation, and in particular, insufficient in suppressing the gradual hemoglobin oxidation after the administration.

Such artificial erythrocytes prepared from hemoglobin are also devoid of 2,3-diphosphoglycerate (2,3-DPG) which is an allosteric effector found in natural erythrocytes, that binds to the hemoglobin to regulate affinity for oxygen of the hemoglobin and enable the efficient transportation of the oxygen by the erythrocytes from lung to peripheral tissues. Consequently, the hemoglobin in the artificial erythrocytes exhibits a quite high affinity for oxygen to result in an insufficient transportation of the oxygen in the body. In view of such situation, various attempts have been made to reduce the oxygen affinity of the free hemoglobin in the artificial erythrocyte. Typical attempts have been chemical binding of pyridoxal phosphate to the hemoglobin and introduction into the hemoglobin molecule of a crosslinking structure. The thus produced modified hemoglobins, however, differ in their molecular structure from the natural hemoglobin, and therefore, may suffer from toxicity or metabolic difficulty. In the liposome-encapsulated hemoglobin, attempts have been made to supplement the hemoglobin solution with 2,3-DPG, or alternatively, with inositol hexaphosphate (hereinafter abbreviated as IHP), which is known to be an allosteric effector in birds.

SUMMARY OF THE INVENTION

In view of such situation, an object of the present invention is to provide a hemoglobin-encapsulated liposome wherein the encapsulated hemoglobin would experience minimized irreversible oxidation into methemoglobin after the administration to a body.

Another object of the present invention is to provide a hemoglobin-encapsulated liposome wherein the hemoglobin would exhibit an appropriately regulated affinity for oxygen, and hence, a high oxygen transportation capacity after its administration.

According to the present invention, there are provided hemoglobin-encapsulated liposomes as described below.

(1) A hemoglobin-encapsulated liposome comprising
a liposome comprising a lipid and an enzymatically active hemoglobin solution encapsulated in said liposome, wherein the hemoglobin solution is supplemented with glucose and at least one member selected from the group consisting of adenine, inosine, and adenosine triphosphate (ATP).

(2) A hemoglobin-encapsulated liposome comprising
a liposome comprising a lipid and an enzymatically active hemoglobin solution encapsulated in said liposome, wherein the hemoglobin solution is supplemented with glucose and adenosine triphosphate.

(3) A hemoglobin-encapsulated liposome comprising
a liposome comprising a lipid and an enzymatically active hemoglobin solution encapsulated in said liposome, wherein the hemoglobin solution is supplemented with glucose, adenine, and inosine.

(4) A hemoglobin-encapsulated liposome comprising a liposome comprising a lipid and an enzymatically active hemoglobin solution encapsulated in said liposome, wherein the hemoglobin solution is supplemented with enzymatic substrates for generating 2,3-diphosphoglycerate.

(5) A hemoglobin-encapsulated liposome comprising a liposome comprising a lipid and an enzymatically active hemoglobin solution encapsulated in said liposome, wherein the hemoglobin solution is supplemented with enzymatic substrates for generating 2,3-diphosphoglycerate and at least one member selected from the group consisting of adenine, inosine, and adenosine triphosphate.

(6) A hemoglobin-encapsulated liposome comprising a liposome comprising a lipid and an enzymatically active hemoglobin solution encapsulated in said liposome, wherein the hemoglobin solution is supplemented with glucose; at least one member selected from the group consisting of adenine, inosine, and adenosine triphosphate; and phosphoenol pyruvate.

Preferred embodiments of the hemoglobin-encapsulated liposome are as described below.

(7) The hemoglobin-encapsulated liposome according to any one of the above (1) to (6) wherein the hemoglobin solution is supplemented with 1 to 30 moles of glucose per 1 mole of the hemoglobin; or with 1 to 300 mM of glucose in terms of molar concentration.

(8) The hemoglobin-encapsulated liposome according to any one of the above (1), (2), (5) and (6) wherein the hemoglobin solution is supplemented with 0.01 to 1 mole of ATP per 1 mole of the hemoglobin; or with 0.01 to 10 mM of ATP in terms of molar concentration.

(9) The hemoglobin-encapsulated liposome according to any one of the above (1), (3), (5) and (6) wherein the hemoglobin solution is supplemented with 0.1 to 10 mole of adenine and 0.01 to 10 mole of inosine per 1 mole of the hemoglobin; or with 0.01 mM to 10 mM of adenine and 0.01 mM to 10 mM of inosine in terms of molar concentration.

(10) The hemoglobin-encapsulated liposome according to any one of the above (4), (5) and (6) wherein the hemoglobin solution is supplemented with 0.05 to 4 moles of phosphoenol pyruvate per 1 mole of the hemoglobin; or 0.05 to 40 mM, and preferably, 1 to 30 mM of phosphoenol pyruvate in terms of molar concentration.

(11) In addition to the components supplemented in the above (7) to (10), the liposomerized hemoglobin solution may be further supplemented with 0.1 to 100 mM of an inorganic phosphate such as $KH_2PO_4$, $Na_2HPO_4$ in terms of molar concentration.

(12) In addition to the components supplemented in the above (7) to (10), the liposomerized hemoglobin solution may be further supplemented with 1 mM to 50 mM of an inorganic salt such as $MgCl_2$ in terms of molar concentration.

(13) In addition to the components supplemented in the above (7) to (10), the liposomerized hemoglobin solution may be further supplemented with 0.05 to 4 moles of an organic phosphate per 1 mole of the hemoglobin. Preferably, the organic phosphate is inositol hexaphosphate (phytic acid).

(14) In the present invention, a method for preparing a hemoglobin-encapsulated liposome according to the above (1) (6) is also provided. The method comprises the steps of:

(a) preparing an enzymatically active concentrated hemoglobin solution having a hemoglobin concentration of from 30 to 60% by weight by subjecting rinsed erythrocytes to hemolysis, removing stroma component, and concentrating the stroma-free hemoglobin solution;

(b) supplementing the concentrated hemoglobin solution with at least one member selected from the group consisting of adenine, inosine, and adenosine triphosphate; and glucose; and optionally, phosphoenolpyruvic acid; and (c) liposomerizing the supplemented hemoglobin solution under mild conditions to prevent enzymes in the hemoglobin solution from losing their activities. Preferably, the liposomerization under mild conditions is conducted by ejecting the hemoglobin solution from an orifice for one to several times at a pressure of 50 to 1,800 kg/cm² at a temperature of below 40° C.

DESCRIPTION OF THE INVENTION

The hemoglobin-encapsulated liposome of the present invention comprises a liposome and an enzymatically active hemoglobin solution encapsulated in said liposome. Preferably, the enzymatically active hemoglobin solution is the one prepared from natural human erythrocytes by the procedure described below.

The enzymatically active hemoglobin solution may be an aqueous hemoglobin solution having a hemoglobin concentration of from 30 to 60% (w/w), and the hemoglobin solution should have at least the glycolysis enzyme activities and methemoglobin reductase such as NADH-cytochrome $b_5$ reductase activities inherited from the natural erythrocytes. The enzymatically active hemoglobin solution should retain at least 50%, and preferably, at least 80% of such enzymatic activities in the natural erythrocytes, from which the hemoglobin solution is derived.

The enzymatically active hemoglobin solution is typically a concentrated stroma-free hemoglobin (SFH) solution prepared by hemolyzing erythrocytes and removing the erythrocyte membrane component therefrom.

More illustratively, the concentrated stroma-free hemoglobin (SFH) solution is prepared by subjecting whole blood to centrifugation to remove plasma components and leave the blood cell (thickened blood cell preparation, or Packed Red Cells); rinsing the blood component fraction by continuous centrifugation with physiological saline to leave erythrocytes and remove other blood components such as platelets and leucocytes; adding water to the rinsed erythrocytes for hemolysis; removing erythrocyte membrane component by applying the resulting component to a plasma separator and a filter to remove the erythrocyte membrane (stroma) and recover stroma-free hemoglobin (SFH) solution; and dyalyzing the resulting SFH solution with a hollow fiber-type dialyzer against pure water and concentrating the resulting product by ultrafiltration.

The resulting the concentrated stroma-free hemoglobin (SFH) solution exhibits glucose metabolysis rate of at least 10% of the natural erythrocytes (thickened blood cell preparation).

The resulting the concentrated stroma-free hemoglobin (SFH) solution also has an activity to produce at least 0.2 mM of ATP when the solution is supplemented with a sufficient amount of adenine, inosine, glucose, NAD, magnesium ion, and phosphate ion.

When the concentrated stroma-free hemoglobin (SFH) solution has enzymatic activities as described above, it should be conceived that equivalent amounts of other glycolysis enzymes and cytochrome $b_5$ reductase enzymes have been inherited from natural erythrocytes.

In the present invention, the liposomerized enzymatically active hemoglobin solution is supplemented with at least one member selected from the group consisting of adenine, inosine, and adenosine triphosphate (ATP); and glucose. If desired, the hemoglobin solution may be further supplemented with phosphoenolpyruvic acid.

With regard to the glucose, the hemoglobin solution may be supplemented with 1 to 30 moles, preferably 2 to 25 moles, and more preferably, 2 to 20 moles of glucose per 1 mole of the hemoglobin. When the amount of glucose added is less than 1 mole per 1 mole of the hemoglobin, conversion of the hemoglobin to methemoglobin would not be sufficiently suppressed. An amount of glucose in excess of 30 moles per 1 mole of hemoglobin will alter flowability of the solution to result in a poor liposomerization efficiency. Addition of the Glucose in the form of D-glucose is preferred.

With regard to the adenine and inosine, the hemoglobin solution may contain 0.1 to 10 mole, preferably 0.1 to 8.5 mole, and more preferably, 0.2 to 5.0 mole of adenine and inosine, respectively, per 1 mole of the hemoglobin. When the amount of either of the adenine or the inosine added is less than 0.1 mole per 1 mole of the hemoglobin, conversion of the hemoglobin to methemoglobin would not be effectively suppressed. An amount of adenine or inosine added in excess of 10 mole per 1 mole of hemoglobin will alter flowability of the solution to result in a poor liposomerization efficiency.

With regard to the ATP, the hemoglobin solution may be supplemented with 0.01 to 1 mole, preferably 0.1 to 1 mole, and more preferably, 0.1 to 0.5 moles of ATP per 1 mole of the hemoglobin. When the amount of ATP is less than 0.01 mole per 1 mole of the hemoglobin, conversion of the hemoglobin to methemoglobin would not be effectively suppressed. An amount of ATP in excess of 1 mole per 1 mole of hemoglobin will alter flowability of the solution to result in a poor liposomerization efficiency. Addition of the ATP in the form of ATP-Na salt is preferred.

With regard to the phosphoenolpyruvic acid, which is a metabolic intermediate that may be added for efficient generation of 2,3-DPG, the hemoglobin solution may be supplemented with 0.01 mM to 200 mM, and preferably, 0.1 mM to 100 mM of phosphoenolpyruvic acid. When the phosphoenolpyruvic acid concentration is less than 0.01 mM, affinity for oxygen would not be satisfactorily regulated. Phosphoenolpyruvic acid concentration in excess of 200 mM will result in a poor liposomerization efficiency.

The enzymatically active hemoglobin solution used in the present invention may be prepared by subjecting the erythrocyte to hemolysis by an ordinary procedure to remove the membrane (stroma), and concentrating the stroma-free hemoglobin (SFH) by filtration through an ultra filtration film having a threshold fractionating molecular weight of 10,000 to a hemoglobin concentration of 30% (w/w) or more. The concentrated SFH solution may be supplemented with malic acid. In the concentrated SFH solution, hemoglobin is in the form of an aqueous solution, and the hemoglobin concentration is preferably in the range of from 30 to 60% (w/w), and more preferably, from 40 to 50% (w/w).

The hemoglobin concentration is adjusted to such range because such range is the highest possible range for the liposomerization of the solution, and the amount of oxygen transported to peripheral tissues would increase in accordance with the increase in the hemoglobin concentration.

The erythrocytes used for the preparation of the stroma-free hemoglobin solution may preferably be of human origin when the resulting hemoglobin-encapsulated liposome is to be administered to human. The erythrocytes used may be those that have been stored for more than 50 days at a temperature below 4° C. after their collection although use of fresh erythrocytes is preferable.

The stroma-free hemoglobin solution prepared under the above-described conditions has glycolysis enzyme activity inherited from the natural erythrocytes, and the hemoglobin solution should have retained at least 50% of the enzymatic activities of the natural erythrocytes when measured at 37° C.

In the present invention, the enzymatically active hemoglobin solution may be additionally supplemented with at least one coenzyme selected from the group consisting of reduced-form nicotinamide adenine dinucleotide (NADH), oxidized-form nicotinamide adenine dinucleotide (NAD), reduced-form nicotinamide adenine dinucleotide phosphate (NADPH), and oxidized-form nicotinamide adenine dinucleotide phosphate (NADP) in addition to the above-described critical reagents.

With regard to such coenzyme, the hemoglobin solution may be supplemented with 0.01 mM to 10 mM of such coenzyme in terms of molar concentration. Addition of the NAD in the form of β-NAD is preferred.

The hemoglobin solution used in the present invention may be additionally supplemented with an organic phosphate compound such as inositol hexaphosphate (IHP) for the purpose of regulating the amount of oxygen released in peripheral tissues. Addition of IHP in the form of phytic acid is preferred.

The hemoglobin solution used in the present invention may be supplemented with an inorganic phosphate compound such as monohydrate or dihydrate of $KH_2PO_4$ or $Na_2HPO_4$. These inorganic phosphates may also be used for the purpose of adjusting the pH of the solution.

Addition of an inorganic salt such as $MgCl_2$ or a hydrate thereof is also preferred for the purpose of providing the magnesium ion required for the enzymatic reaction.

The lipid used for the formation of the liposome is not limited to any particular type so long as it is capable of forming the liposome, and both natural and synthetic lipids may be used for such a purpose. Exemplary lipids include lecithin (phosphatidylcholine), phosphatidylethanolamine, phosphatidic acid, phosphatidylserine, phosphatidylinositol, phosphatidylglycerol, sphingomyelin, cardiolipin, and hydrogenated derivatives thereof, which may be used either alone or in combination of two or more.

In the present invention, a charge donor, for example, a sterol or a fatty acid may be added as a component of the liposome membrane to strengthen the film and to adjust the period required for digestion after its administration.

The liposome of the present invention may have added thereto a tocopherol analogue, namely, vitamin E in order to prevent oxidation. Tocopherol has four isomers, $\alpha$, $\beta$, $\gamma$, and $\delta$, and any of them may be used in the present invention. The tocopherol may be added in an amount of from 0.5 to 4.5% by mole, and preferably, from 1.0 to 2.0% by mole per total amount of the lipid.

The hemoglobin-encapsulated liposome of the present invention may be produced by subjecting rinsed erythrocytes to hemolysis; removing erythrocyte membrane component; concentrating the hemoglobin solution to 30 to 60% (w/w); supplementing the concentrated hemoglobin solution with glucose, adenine and inosine, or with glucose and ATP, or with glucose, adenine, inosine, and ATP, and stirring the solution; and liposomerizing the solution by subjecting the solution to high-pressure injection treatment under mild conditions to prevent the enzymes in the hemoglobin solution from losing their enzymatic activity.

Such liposomerization under mild conditions may be conducted by ejecting the hemoglobin solution for once to several times from an orifice at a pressure of from 50 to 1,800 kg/cm$^2$, and preferably, from 80 to 1,200 kg/cm$^2$. The temperature is maintained during the liposomerization at 40° C. or less. For example, the liposomerization may be carried out at a pressure of from 480 to 1,450 kg/cm$^2$ when the high-pressure injection emulsifier used is microfluidizer 100Y (Microfluidizer Co.), or at a pressure of from 80 to 200 kg/cm$^2$ when Parr cell disruptor (Parr Co.) is used. In either case, the liposomerization is to be carried out at a temperature of below 40° C., and preferably, below 0° C.

In natural erythrocytes, hemoglobin is gradually converted to methemoglobin by oxidation, and in turn, the methemoglobin is reduced to hemoglobin by the action of enzymes in the erythrocytes, and hemoglobin thereby undergoes a reversible hemoglobin-methemoglobin reaction. More illustratively, in natural erythrocytes, conversion of hemoglobin to methemoglobin accompanies reduction of NAD and NADP, and NADH and NADPH are thereby produced. The thus produced NADH and NADPH are then reversibly oxidized simultaneously with the reduction of the methemoglobin to the hemoglobin. NADH-cytochrome b$_5$ reductase system is involved in such reversible hemoglobin-methemoglobin reaction.

The hemoglobin taken out of the natural erythrocyte is devoid of such methemoglobin reduction system, and the hemoglobin once converted to methemoglobin is not reduced to hemoglobin, and the hemoglobin thereby loses its oxygen-transportation capacity.

The inventors of the present invention have estimated that inactivation of the enzymes involved in the methemoglobin reduction by physical energy or heat applied upon liposomerization of the hemoglobin solution should be responsible for such irreversible conversion of the hemoglobin to the methemoglobin. Based on such estimation, the inventors prepared hemoglobin-encapsulated liposomes by conducting the liposomerization under various mild conditions to retain the enzymatic activity of the hemoglobin solution. However, even when the liposomerization was carried out by ejecting the hemoglobin solution from the orifice for one to several times at a pressure as low as 50 to 1,600 kg/cm$^2$, and preferably, at 80 to 1,200 kg/cm$^2$, the hemoglobin-encapsulated liposome prepared underwent gradual oxidation of the encapsulated hemoglobin after its administration.

After intensive investigations, the inventors of the present invention have found that the hemoglobin oxidation that gradually takes place after the administration of the liposomerized hemoglobin may be significantly suppressed by adding glucose, adenine and inosine; glucose and ATP; or glucose, adenine, inosine and ATP to the hemoglobin solution that had been prepared under mild conditions.

A deduced mechanism for such oxidation suppression is as described below. When the hemoglobin solution is liposomerized under the mild conditions as described above, the hemoglobin solution would not lose its enzymatic activities. However, substrates for the enzymatic reactions and coenzymes having a molecular weight of up to 10,000 would have been removed in the course of the removal of the membrane component for collecting the hemoglobin solution and the subsequent purification and concentration of the hemoglobin solution. As a consequence, no methemoglobin-reducing reaction would occur in the resulting hemoglobin solution. When glucose together with adenine and inosine that are required for the production of ATP; glucose together with ATP; or glucose together with adenine, inosine, and ATP are added to the enzymatically active hemoglobin solution, the ATP produced from adenine, inosine and inorganic phosphate or the ATP added as well as NAD will serve coenzymes for the glycolysis pathway from the glucose (glycolysis enzyme), and the thus induced glycolysis will result in the reduction from NAD and NADP to NADH and NADPH, respectively, as in the case of the natural erythrocyte. Methemoglobin generated in the liposomerized hemoglobin solution will then be reduced by the NADH-cytochrome b$_5$ reductase. Irreversible oxidation of the hemoglobin that gradually proceeds in the liposome is thereby suppressed.

In natural erythrocytes, 2,3-DPG is present at a concentration of 80 to 100 µg/ml of blood and the concentration is maintained at a substantially constant level. 2,3-DPG strongly binds with the hemoglobin to maintain the affinity for oxygen of the hemoglobin at a level of 27 to 30 mmHg in terms of p50, which is oxygen partial pressure when the oxygen fractional saturation is 50%. Transportation of oxygen from lung to peripheral cells by the erythrocytes is thereby efficiently conducted. Furthermore, since 2,3-DPG preferentially binds to deoxyhemoglobin, O$_2$ dissociation curve will represent the sigmoid shape characteristic to natural erythrocytes by the allosteric effects, and homeostasis of the body is maintained by the sensitively altered oxygen transportation efficiency in response to the oxygen partial pressure in veins. The blood after long-term storage and the stroma-free hemoglobin solution are substantially free from such 2,3-DPG, and consequently, they suffer from unduly high oxygen affinity to become incapable of efficiently transporting the oxygen.

The inventors of the present invention have carried out an intensive investigation, and found that liposomerization of the hemoglobin solution under mild conditions that would not result in the inactivation of the enzymes involved in the glycolysis pathway in natural erythrocytes, and addition to the hemoglobin solution of enzyme substrates in the glycolysis pathway should result in the hemoglobin-encapsulated liposomes having oxygen transportation capacity equivalent to or higher than natural erythrocytes.

A deduced mechanism for such improvement in the oxygen transportation capacity is as described below. When the hemoglobin solution is liposomerized under the mild conditions as described above, the hemoglobin solution would not lose its enzymatic activity. However, substances required for enzymatic reactions such as substrates for the enzymatic reactions and coenzymes having a molecular weight of up to 10,000 would have been removed in the course of the removal of the membrane component for collecting the hemoglobin solution and the subsequent purification and concentration of the hemoglobin solution. When such hemoglobin solution is liposomerized with no supplementation of other substances, glycolysis would not occur in the resulting liposomes, and 2,3-DPG, which should be produced in course of the glycolysis, would not be produced. When the hemoglobin solution is supplemented with glucose, adenine, inosine, phosphoenol pyruvate, and an inorganic phosphate, ATP would be produced from the adenine, inosine, and inorganic phosphate, and the thus produced ATP and the optionally supplemented NAD would participate in the glycolysis pathway as coenzymes. As a result, 2,3-DPG would be produced in the liposomes, and the hemoglobin-encapsulated liposomes would exhibit regulated affinity for oxygen. Furthermore, when the hemoglobin solution is supplemented with phosphoenol pyruvate which is a metabolic intermediate in the glycolysis pathway to increase the concentration of the phosphoenol pyruvate, glycolysis in reverse direction would also be induced to result in an increased generation of the 2,3-DPG, leading to an increased oxygen transportation efficiency. In such case, reduction from NAD to NADH would also be induced, and the methemoglobin produced in the liposome would be reduced to hemoglobin by the NADH-cytochrome $b_5$ reductase. The hemoglobin oxidation that gradually proceeds in the liposomes is thereby suppressed.

The above-described glycolysis enzymatic activities of the hemoglobin solution that had been inherited from natural erythrocytes have been conventionally regarded as impurities. The inventors of the present invention have efficiently utilized such glycolysis enzymatic activities of the hemoglobin solution by supplementing the enzymatic substrates and the coenzymes necessary for activating the glycolysis pathway, and succeeded in generating the 2,3-DPG in the liposomes as in the natural erythrocytes. The hemoglobin-encapsulated liposome having appropriately regulated affinity for oxygen of the present invention was thereby obtained.

The present invention is described in further detail by referring to the following Examples and Comparative Examples.

EXAMPLES

It should be noted that, unless otherwise noted, various stages of the preparation were aseptically carried out under the cooled conditions of 4° C. The reagents and instruments used had been sterilized, and an aseptic ultra-pure water (at least 15 megΩ·C·cm at 25° C., pyrogen free) containing no residual heavy metal ions or inorganic ions was used for the preparation.

Example 1

(1) Preparation of Concentrated Stroma-free Hemoglobin (SFH) Solution 15 liters of thickened erythrocytes (Packed Red Cells manufactured by the Japanese Red Cross Society) were rinsed with physiological saline using continuous flow centrifuge to remove platelets, leukocytes and other components that had been included in the plasma with the erythrocytes to obtain rinsed erythrocytes. To 5 liters of the rinsed erythrocytes was added 10 liters of pure water for hemolysis. The resulting product was applied to a plasma separator having a pore size of 0.45 μm, and then, to a filter having a threshold fractionating molecular weight of 300,000 having a pore diameter of 5 nm to remove erythrocyte membrane (stroma) to recover 12 liters of stroma-free hemoglobin (SFH) solution having a hemoglobin concentration of 8% (w/v). The resulting SFH solution was adjusted to pH 7.4 by adding sodium bicarbonate. The resulting solution was dialyzed with a hollow fiber-type dialyzer (CL-C8N, Terumo Corporation) against pure water, and the concentrated by ultrafiltration to obtain 1.8 liters of SFH solution having a hemoglobin concentration of 50% (w/v).

(2) Supplementation of the Concentrated SFH Solution

To 200 ml of the concentrated SFH solution prepared in the above-described step (1) were added β-NAD (1 mM, 133 mg), D-glucose (100 mM, 3.6 g), ATP-Na (1 mM, 110 mg), magnesium chloride hexahydrate (1 mM, 40 mg), dipotassium hydrogen phosphate (9 mM, 247 mg), disodium hydrogen phosphate (11 mM, 310 mg), and phytic acid (3 mM, 396 mg), and the mixture was stirred until the reagents added were homogeneously incorporated in the hemoglobin solution.

(3) Encapsulation of the Supplemented Concentrated SFH Solution in Liposome

To 45 grams of a uniformly mixed powder comprising purified phosphatydylchorine (HSPC) from soy bean having hydrogenation rate of 90%, cholesterol (Chol), myristic acid (MA) and tocopherol (TOC) in a HSPC:Chol:MA:Toc molar ratio of 7:7:2:0.28 was added 45 ml of pure water, and the mixture was heated to a temperature of from 60° to 70° C. to allow for swelling. To the thus swelled starting lipid material was added the mixed solution prepared in the above-described step (2), and the mixture was agitated for 15 seconds. The thus prepared lipid-SFH mixed solution was fed to Microfluidizer 110Y (Microfluidics Co.) and liposomerization was conducted in an ice bath at a pressure of 12,000 psi (about 844 kg/cm$^2$).

(4) Purification of the Hemoglobin-encapsulated Liposome

To the product of the above-described step (3) was added an equal volume of physiological saline having dextran (3% (w/v)) added thereto, and the resulting suspension was subjected to centrifugation at 10,000 rpm (13,000 g)×30 min. at 4° C. The liposomes having the hemoglobin solution encapsulated therein were collected as centrifugate at a high efficiency. The supernatant containing the residual free hemoglobin that failed to be encapsulated as well as the starting lipid components were removed by decantation or suction. The above-described washing process was repeated until no free hemoglobin was recognized in the supernatant with naked eye. The resulting product was filtered through Durapore membrane filter (Minitan System, Millipore Ltd.) having a pore size of 0.45 μm to remove coarse particles in the suspension. The filtrate was subjected to ultrafiltration through a hollow fiber-type dialyzer (CL-C8N, manufactured by Terumo Corporation) for concentration to produce 600 ml of purified hemoglobin-encapsulated liposome suspension having a hemoglobin concentration of 5% (w/v).

Example 2

To 200 ml of the concentrated SFH solution prepared in Example 1(1) was added β-NAD (1 mM, 133 mg), D-glucose (100 mM, 3.6 g), adenine (2 mM, 54 mg), inosine (5 mM, 268 mg), magnesium chloride hexahydrate (1 mM, 40 mg), dipotassium hydrogen phosphate (9 mM, 247 mg), disodium hydrogen phosphate (11 mM, 310 mg), and phytic acid (3 mM, 396 mg), and the mixture was stirred until the reagents added were homogeneously incorporated in the hemoglobin solution. The procedure of Example 1(3) and 1(4) was repeated for liposomerization of the supplemented hemoglobin solution, and purification and concentration of the resulting liposome suspension to produce 600 ml of purified hemoglobin-encapsulated liposome suspension having a hemoglobin concentration of 5% (w/v).

Comparative Example 1

The procedure of Example 1 was repeated except that only the phytic acid (3 mM, 396 mg) was added to the concentrated SFH solution prepared in Example 1(1). After the liposomerization of the supplemented hemoglobin solution, and the purification and concentration of the resulting liposome suspension, there was produced 600 ml of control purified hemoglobin-encapsulated liposome suspension having a hemoglobin concentration of 5% (w/v).

The hemoglobin-encapsulated liposome suspensions obtained in Examples 1 and 2 and Comparative Example 1 were evaluated for their ATP content and susceptibility for in vivo oxidation in Experiments 1 and 2 as described below.

Experiment 1

Figure 1:
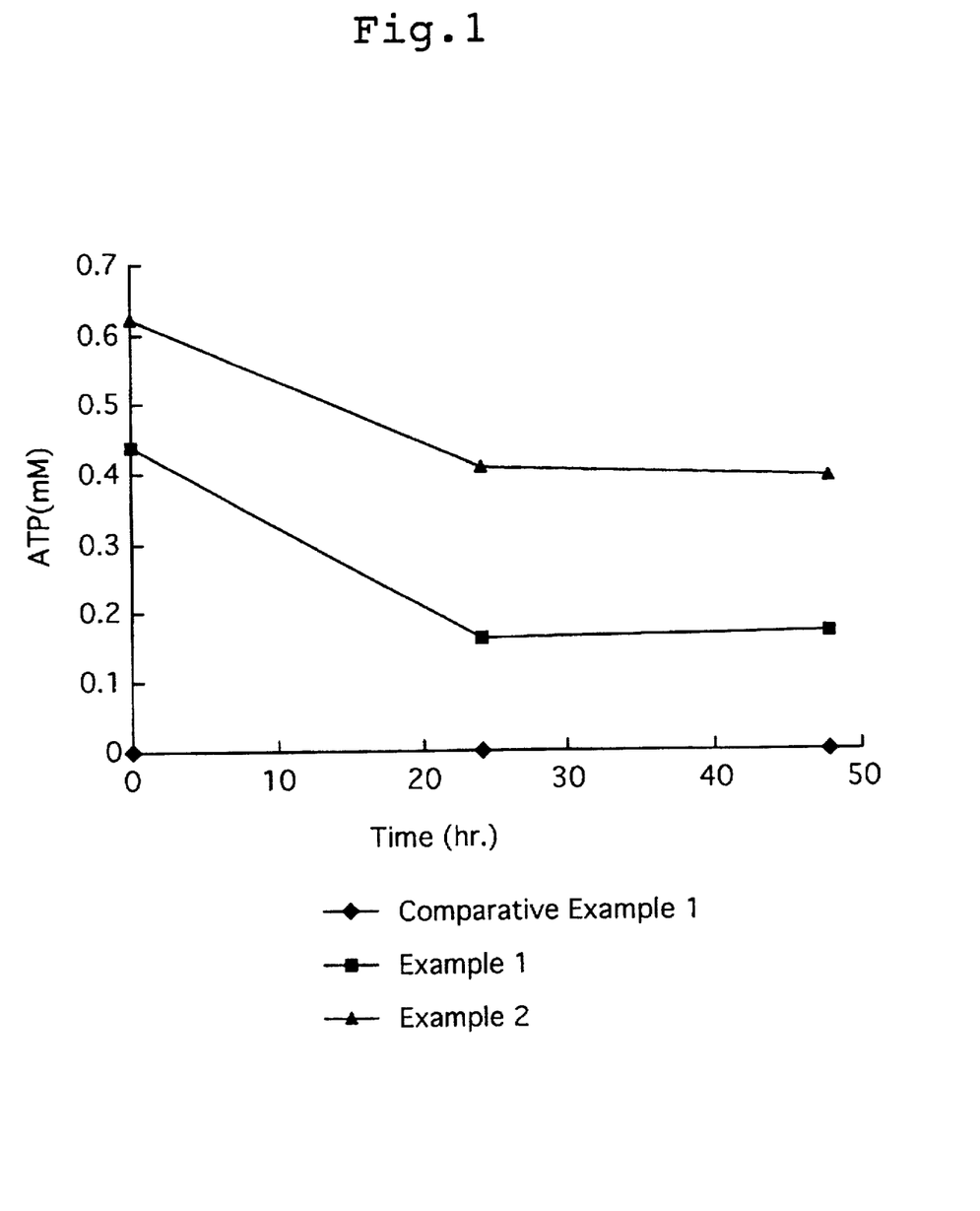
FIG. 1 diagrammatically shows measurements for the concentration of the ATP in the liposome.

Measurement of the Amount of ATP in the Liposome 10 ml of the hemoglobin-encapsulated liposome suspension was incubated at 37° C., and 0.5 ml sample was collected after a predetermined period. To the sample was added 2 ml of 10% (w/v) Triton×100—HEPES buffer (0.5M, pH 7.4), and the mixture was agitated. To the mixture was also added Freon, and the mixture was agitated for another about 1 minute. The resulting solution was centrifuged at 3,000 rpm for 15 minutes, and 1.8 ml of the supernatant was passed through a ultrafiltration membrane having a threshold fractionating molecular weight of 5,000 to remove the protein molecules. The protein free solution was evaluated for its ATP concentration by subjecting the solution to high-speed liquid chromatography utilizing ODS column (ODS-1301-N, Senshu Kagaku K.K.). The results are depicted in FIG. 1.

Experiment 2

Measurement of Gradual Conversion of the Liposomerized Hemoglobin to Methemoglobin (in vivo)

To male ICR mouse of 5 week old was administered 1 ml of the hemoglobin-encapsulated liposome suspension having the hemoglobin concentration of 5% (w/v) from its tail vein. After 24 hours, whole blood was collected from its abdominal large vein, and oxidation rate was calculated by the procedure as described below.

The hemoglobin-encapsulated liposomes are more resistant to change in osmotic pressure than natural erythrocytes, and separation of the hemoglobin-encapsulated liposomes from the natural erythrocytes was carried out by utilizing such difference. More illustratively, to the collected whole blood having added heparin thereto was added 8 to 10 volumes of pure water and the mixture was agitated to promote the hemolysis of the natural mouse erythrocytes. The mixture was then subjected to a high-speed centrifugation at 18,000 rpm for 30 minutes at 4° C. to collect the hemoglobin-encapsulating liposomes as the centrifugate.

The above-described procedure was repeated for 3 times to completely wash off the blood components from the sample. To the thus obtained sample was added 2 ml of 10% (w/v) Triton×100—HEPES buffer (0.5M, pH 7.4), and the mixture was agitated. To the mixture was also added 2 ml of Freon, and the mixture was agitated for another about 1 minute. The resulting solution was centrifuged at 3,000 rpm for 15 minutes, and 1 ml of HEPES buffer was added to about 1.8 ml of the supernatant. The resulting mixture was evaluated for its absorption spectrum in the visible range (700 nm to 460 nm) to calculate the rate of oxidation.

Figure 2:
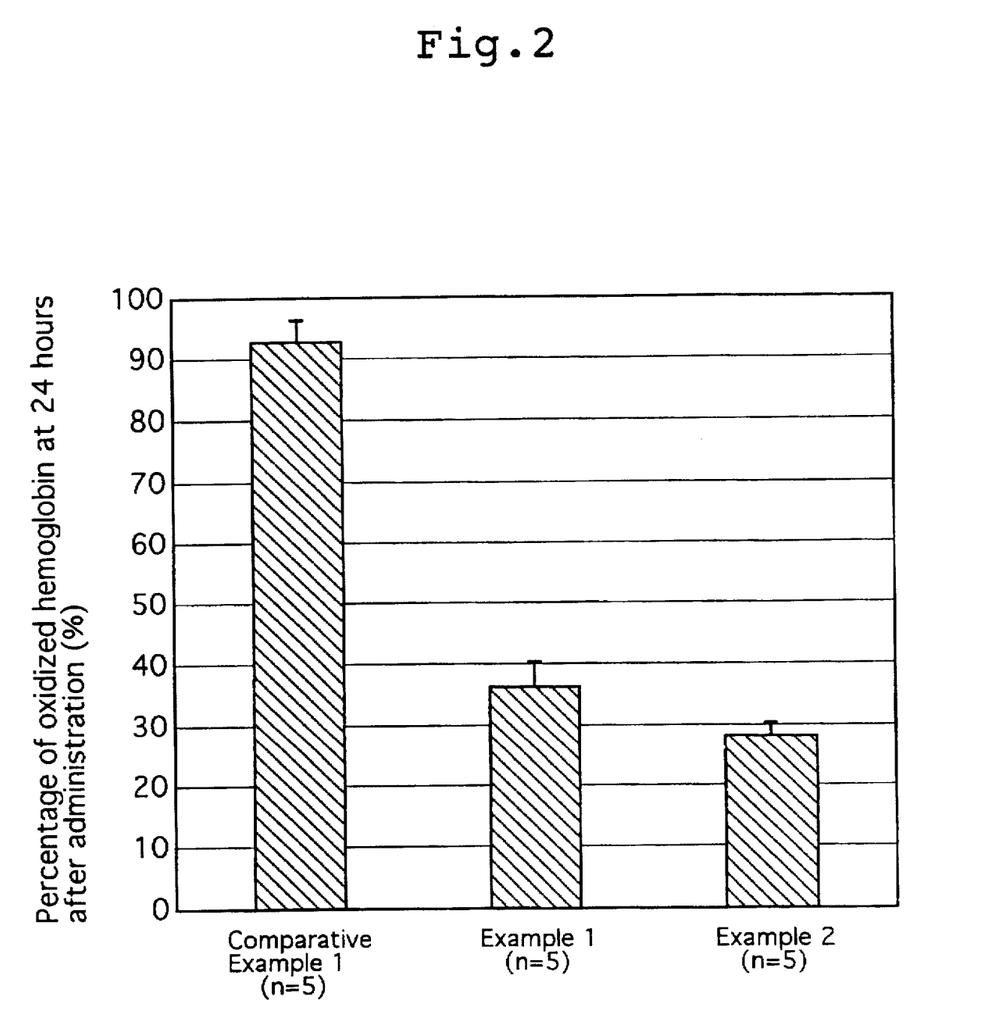
FIG. 2 diagrammatically shows measurements for the oxidation of the hemoglobin into methemoglobin in the liposome.

The results are shown in Table 1 and FIG. 2.

TABLE 1

| Sample | Oxidized hemoglobin, % | |
|---|---|---|
| | Before the administration | 24 hr after the administration |
| Comparative Example 1 (n = 15) | | |
| Mean | 5.6 | 91.6 |
| S.D. | ±4.4 | ±4.8 |
| Example 1 (n = 5) | | |
| Mean | 0 | 35.8 |
| S.D. | | ±4.31 |
| Example 2 (n = 5) | | |
| Mean | 0 | 27.1 |
| S.D. | | ±3.56 |

S.D.: Standard deviation

Example 3

To 200 ml of the concentrated SFH solution prepared in Example 1(1) was added β-NAD (1 mM, 133 mg), D-glucose (100 mM, 3.6 g), adenine (2 mM, 54 mg), inosine (5 mM, 268 mg), magnesium chloride hexahydrate (1 mM, 40 mg), dipotassium hydrogen phosphate (9 mM, 247 mg), and disodium hydrogen phosphate (11 mM, 310 mg), and the mixture was stirred until the reagents added were homogeneously incorporated in the hemoglobin solution. The procedure of Example 1(3) and 1(4) was repeated for liposomerization of the supplemented hemoglobin solution, and purification and concentration of the resulting liposome suspension to produce 600 ml of purified hemoglobin-encapsulated liposome suspension having a hemoglobin concentration of 5% (w/v).

Example 4

To 200 ml of the concentrated SFH solution prepared in Example 1(1) was added β-NAD (1 mM, 133 mg), D-glucose (100 mM, 3.6 g), adenine (2 mM, 54 mg), inosine (5 mM, 268 mg), phosphoenolpyruvic acid (5 mM, 234 mg), magnesium chloride hexahydrate (1 mM, 40 mg), dipotassium hydrogen phosphate (9 mM, 247 mg), and disodium hydrogen phosphate (11 mM, 310 mg), and the mixture was stirred until the reagents added were homogeneously incorporated in the hemoglobin solution. The procedure of Example 1(3) and 1(4) was repeated for liposomerization of the supplemented hemoglobin solution, and purification and concentration of the resulting liposome suspension to produce 600 ml of purified hemoglobin-encapsulated liposome suspension having a hemoglobin concentration of 5% (w/v).

Example 5

To 200 ml of the concentrated SFH solution prepared in Example 1(1) was added β-NAD (1 mM, 133 mg), D-glucose (100 mM, 3.6 g), adenine (2 mM, 54 mg), inosine (5 mM, 268 mg), phosphoenolpyruvic acid (10 mM, 468 mg), magnesium chloride hexahydrate (1 mM, 40 mg), dipotassium hydrogen phosphate (9 mM, 247 mg), and disodium hydrogen phosphate (11 mM, 310 mg), and the mixture was stirred until the reagents added were homogeneously incorporated in the hemoglobin solution. The procedure of Example 1(3) and 1(4) was repeated for liposomerization of the supplemented hemoglobin solution, and purification and concentration of the resulting liposome suspension to produce 600 ml of purified hemoglobin-encapsulated liposome suspension having a hemoglobin concentration of 5% (w/v).

Example 6

To 200 ml of the concentrated SFH solution prepared in Example 1(1) was added β-NAD (1 mM, 133 mg), D-glucose (100 mM, 3.6 g), adenine (2 mM, 54 mg), inosine (5 mM, 268 mg), phosphoenolpyruvic acid (20 mM, 936 mg), magnesium chloride hexahydrate (1 mM, 40 mg), dipotassium hydrogen phosphate (9 mM, 247 mg), and disodium hydrogen phosphate (11 mM, 310 mg), and the mixture was stirred until the reagents added were homogeneously incorporated in the hemoglobin solution. The procedure of Example 1(3) and 1(4) was repeated for liposomerization of the supplemented hemoglobin solution, and purification and concentration of the resulting liposome suspension to produce 600 ml of purified hemoglobin-encapsulated liposome suspension having a hemoglobin concentration of 5% (w/v).

Comparative Example 2

The procedure of Example 1 was repeated except that no reagent was added to the concentrated SFH solution prepared in Example 1(1). After the liposomerization of the supplemented hemoglobin solution, and the purification and concentration of the resulting liposome suspension, there was produced 600 ml of control purified hemoglobin-encapsulated liposome suspension having a hemoglobin concentration of 5% (w/v).

Figure 3:
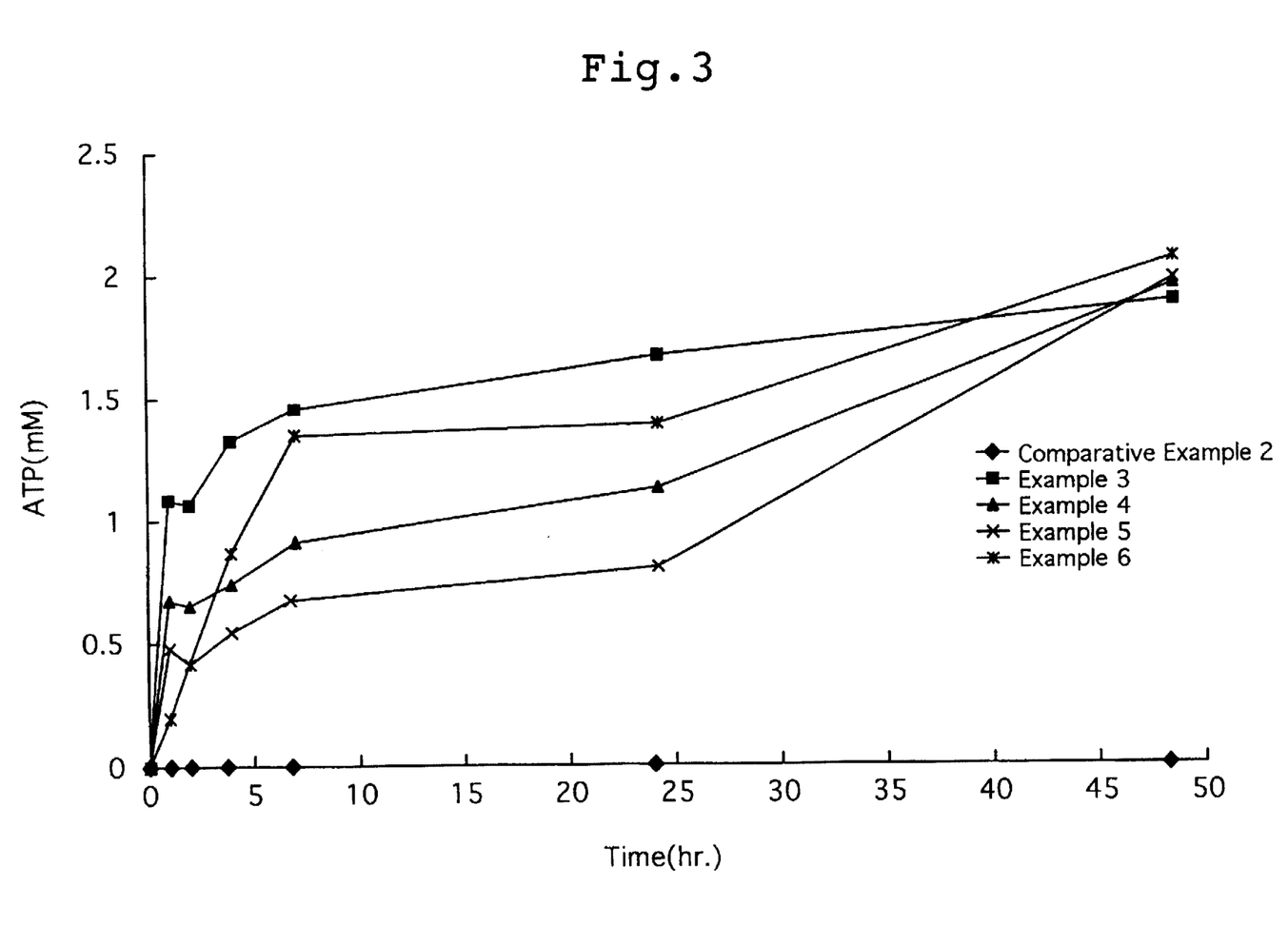
FIG. 3 diagrammatically shows measurements for the concentration of the ATP in the liposome.

The hemoglobin-encapsulated liposome suspensions obtained in Examples 3 to 6 and Comparative Example 2 were evaluated for their ATP content in accordance with the procedure described in the above-described Experiment 1. The results are shown in FIG. 3. The hemoglobin-encapsulated liposome suspensions were also evaluated for their content of 2,3-DPG, affinity for oxygen, and susceptibility for in vitro oxidation in Experiment 3, 4 and 5 as described below.

Experiment 3

Figure 4:
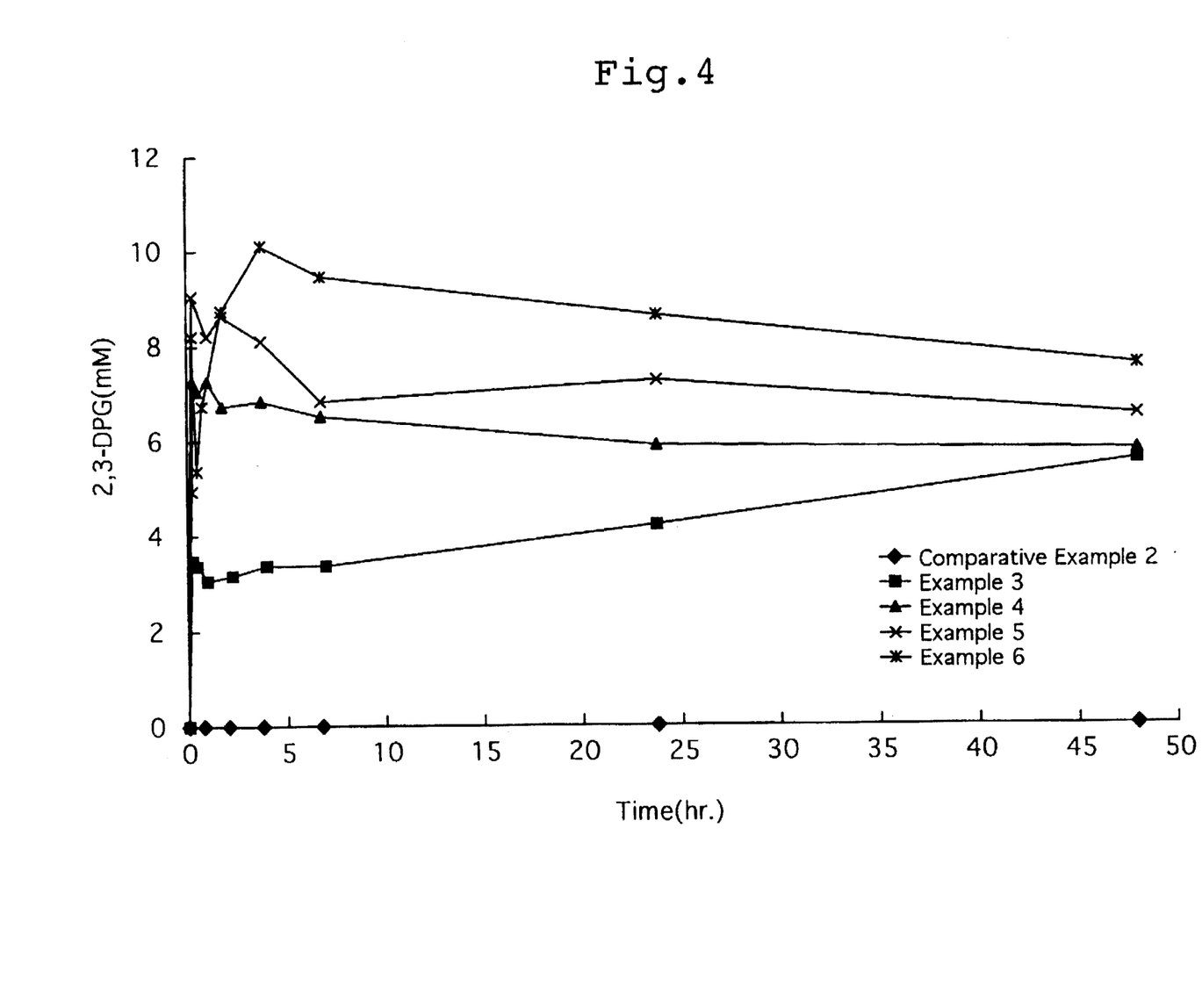
FIG. 4 diagrammatically shows measurements for the concentration of the 2,3-DPG in the liposome.

Measurement of the Amount of 2,3-DPG in the Liposome 10 ml of the hemoglobin-encapsulated liposome suspension was incubated at 37° C., and 0.5 ml sample was collected after predetermined periods. To the sample was added 2 ml of 10% (w/v) Tritonx100—HEPES buffer (0.5M, pH 7.4), and the mixture was agitated. To the mixture was also added 2 ml of Freon, and the mixture was agitated for another about 1 minute. The resulting solution was centrifuged at 3,000 rpm for 15 minutes, and 1.8 ml of the supernatant was passed through a ultrafiltration membrane having a threshold fractionating molecular weight of 5,000 to remove the protein molecules. The resulting protein free solution was evaluated for its 2,3-DPG concentration by subjecting the solution to 2,3-DPG test (BMY, Berlinger-Menheim). The results are depicted in FIG. 4.

Experiment 4

Measurement of Oxygen Affinity (p50) of the Liposomerized Hemoglobin

Figure 5:
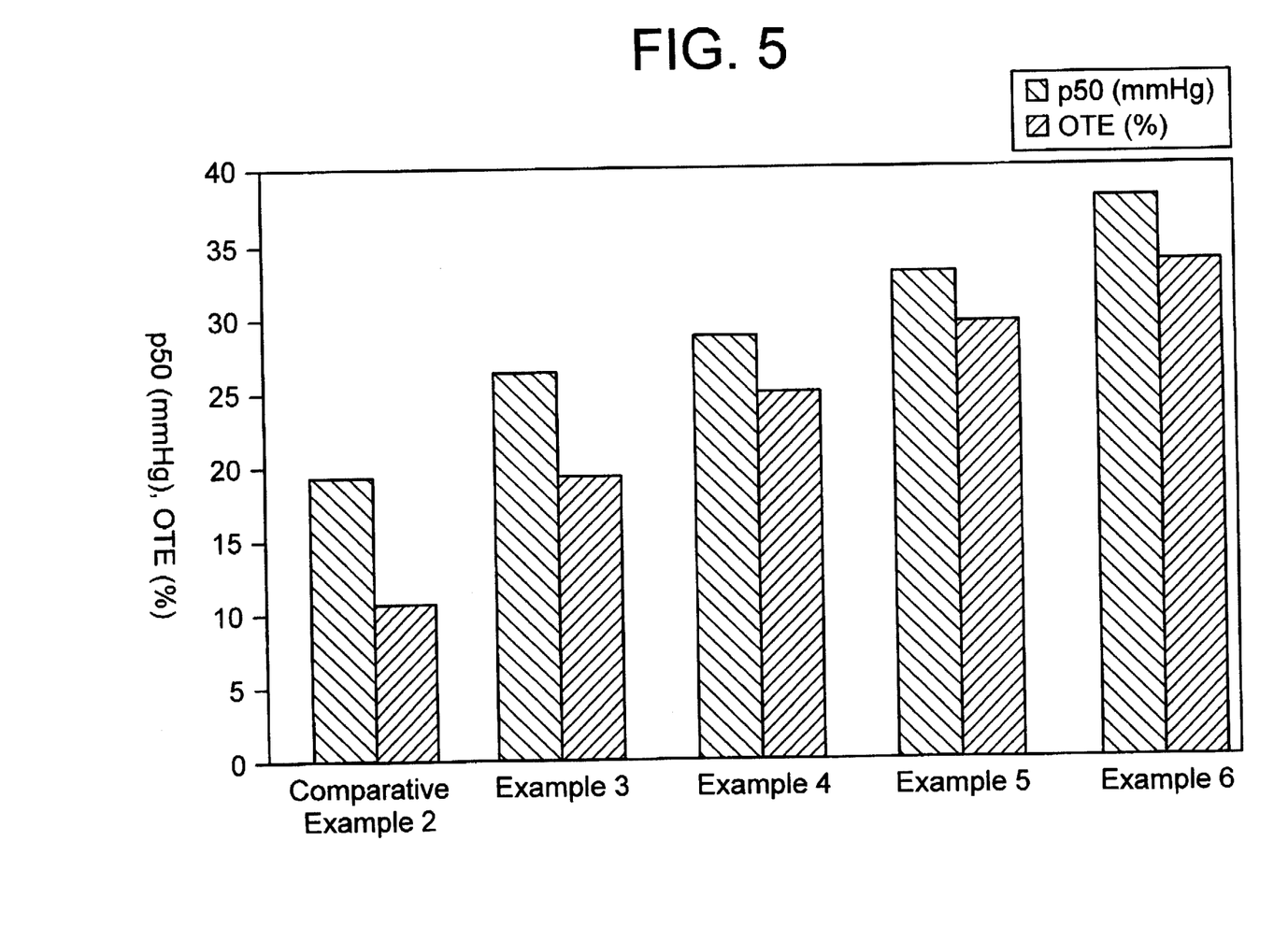
FIG. 5 diagrammatically shows measurements for the oxygen affinity (p50) of the liposomerized hemoglobin.

The hemoglobin-encapsulated liposome suspension was further suspended in phosphate buffer, pH 7.4 at 37° C. ($pCO_2$=40 mmHg) to a hemoglobin concentration of 0.05% (w/v), and absorption spectrum upon alteration of oxygen partial pressure $pO_2$ from 300 mmHg to 0 mmHg ($pCO_2$=40 mmHg) was measured to calculate oxygen fractional saturation, oxygen affinity, p50 (oxygen partial pressure, $pO_2$ when the oxygen fractional saturation is 50%), and oxygen transportation efficiency, OTE (percentage of the hemoglobin that transports the oxygen when the $pO_2$ in the lung is 100 mmHg and the $pO_2$ of the peripheral tissue is 40 mmHg). The results are shown in Table 2 and FIG. 5.

TABLE 2

|  | p50, mm Hg | OTE, % |
| --- | --- | --- |
| Comparative Example 2 | 19.3 | 10.4 |
| Example 3 | 26.0 | 18.9 |
| Example 4 | 28.1 | 24.4 |
| Example 5 | 32.2 | 29.1 |
| Example 6 | 37.4 | 33.0 |

Experiment 5

Measurement of Gradual Conversion of the Liposomerized Hemoglobin to Methemoglobin 1 ml of the hemoglobin-encapsulated liposome suspension having the hemoglobin concentration of 5% (w/v) was incubated at 37° C. for 24 hours, and oxidation rate was calculated as described below.

Figure 6:
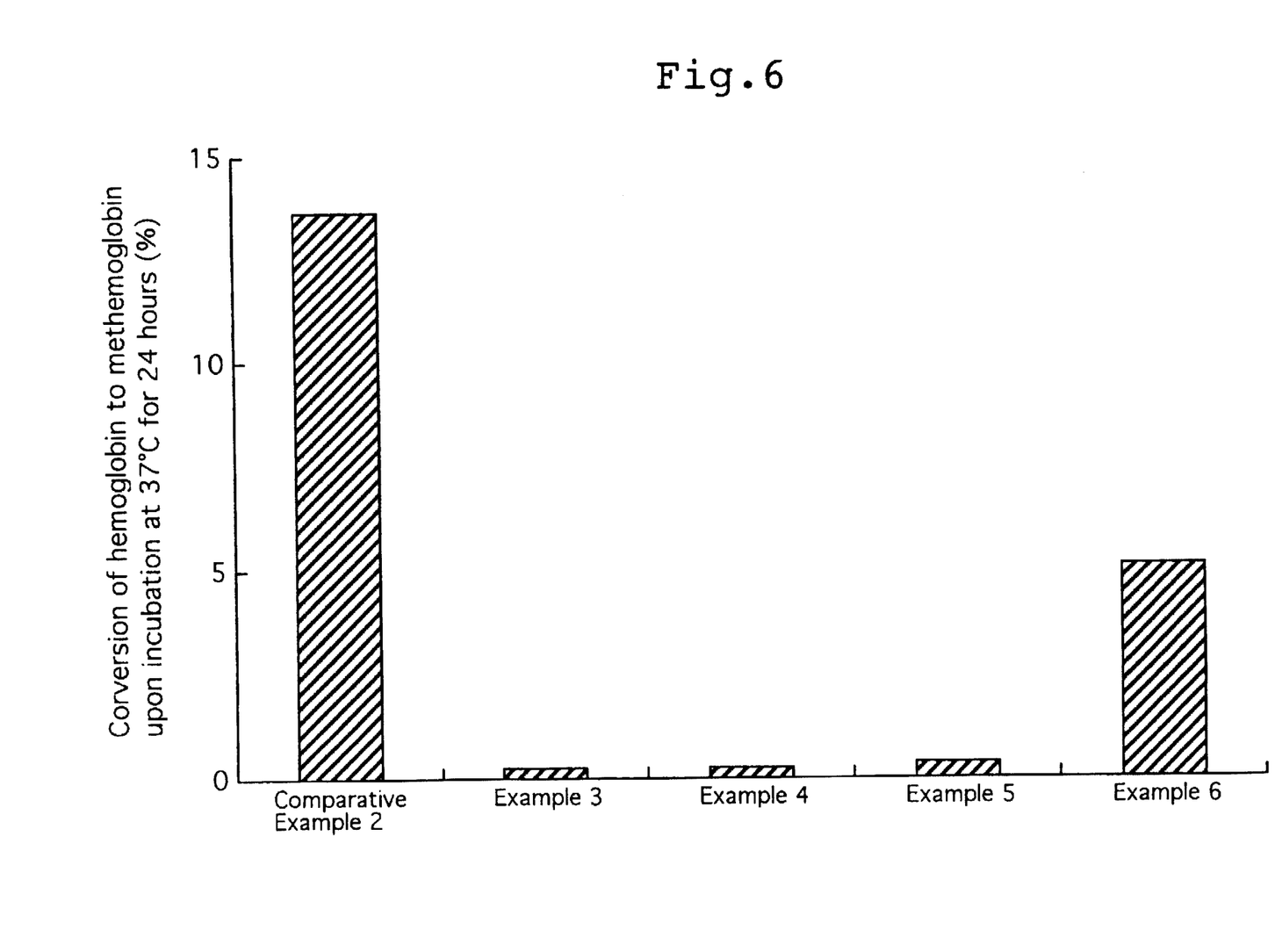
FIG. 6 diagrammatically shows measurements for the oxidation of the hemoglobin into methemoglobin in the liposome.

To the incubated sample was added 2 ml of 10% (w/v) Tritonx100—HEPES buffer (0.5M, pH 7.4), and the mixture was agitated. To the mixture was also added 2 ml of Freon, and the mixture was agitated for another about 1 minute. The resulting solution was centrifuged at 3,000 rpm for 15 minutes, and 1 ml of HEPES buffer was added to about 1.8 ml of the supernatant. The resulting mixture was evaluated for its absorption spectrum in the visible range (700 nm to 460 nm) to calculate the rate of oxidation. The results are shown in FIG. 6.

Merits of the Invention

The hemoglobin-encapsulated liposome of the present invention is produced by preparing a hemoglobin solution wherein the enzymatic activities of the natural erythrocytes are conserved, and encapsulating the thus prepared enzymatically active hemoglobin solution in the liposome under mild conditions without impairing its enzymatic activities. In addition, the liposomerized enzymatically active hemoglobin solution is supplemented with an enzymatic substrate and a coenzyme, and optionally, further with a metabolic intermediate, which are required for metabolysis.

Therefore, glucose is metabolyzed at a high efficiency owing to the abundant ATP, and in course of the glycolysis, NADH and NADPH that had generated with the conversion of the hemoglobin into methemoglobin are oxydized to NAD or NADP simultaneously with the reduction of the methemoglobin back to the hemoglobin. Accordingly, the hemoglobin-encapsulated in the hemoglobin-encapsulated liposome of the present invention exhibits an improved resistance to irreversible convertion into methemoglobin.

Furthermore, in the hemoglobin-encapsulated liposome of the present invention, 2,3-DPG is metabolically generated at a high efficiency to realize an adequately regulated affinity for oxygen.

As described above, the hemoglobin-encapsulated liposome of the present invention has an adequately regulated affinity for oxygen as well as an improved resistance to irreversible conversion to methemoglobin, and consequently, may serve a useful artificial erythrocyte.

We claim:

1. A stable hemoglobin-encapsulated liposome comprising
   a liposome comprising a lipid, and
   a hemoglobin-containing solution which comprises a concentrated stroma-free hemoglobin solution derived from natural erythrocyte to which has been added a stabilizing effective amount of glucose and at least one member selected from the group consisting of adenine, inosine, and adenosine triphosphate.

2. The hemoglobin-encapsulated liposome according to claim 1, wherein said addition of glucose reduces the methemo-globin produced in the liposome to hemoglobin.

3. The hemoglobin-encapsulated liposome according to claim 1, wherein
   said hemoglobin-containing solution comprises a stabilizing effective amount of glucose and adenosine triphosphate.

4. The hemoglobin-encapsulated liposome according to claim 1, wherein
   said hemoglobin-containing solution comprises a stabilizing effective amount of glucose, adenine, and inosine.

5. The hemoglobin-encapsulated liposome according to claim 1, wherein said hemoglobin-containing solution further comprises phosphoenol pyruvate.

6. The hemoglobin-encapsulated liposome according to claim 4, wherein said hemoglobin-containing solution further comprises phosphoenol pyruvate.

7. The hemoglobin-encapsulated liposome according to claim 1, wherein said hemoglobin-containing solution further comprises at least one member selected from the group consisting of reduced-form nicotinamide adenine dinucleotide, oxidized-form nicotinamide adenine dinucleotide, reduced-form nicotinamide adenine dinucleotide phosphate, and oxidized-form nicotinamide adenine dinucleotide phosphate.

8. The hemoglobin-encapsulated liposome according to claim 5, wherein said hemoglobin-containing solution further comprises at least one member selected from the group consisting of reduced-form nicotinamide adenine dinucleotide, oxidized-form nicotinamide adenine dinucleotide, reduced-form nicotinamide adenine dinucleotide phosphate, and oxidized-form nicotinamide adenine dinucleotide phosphate.

9. A method for preparing a hemoglobin-encapsulated liposome according to claim 1, comprising the steps of
   (a) preparing a hemoglobin-containing solution comprising a concentrated stroma-free hemoglobin solution derived from natural erythrocyte having a hemoglobin concentration ranging from 30 to 60% by weight by subjecting rinsed erythrocytes to hemolysis, removing stroma component, and concentrating the stroma-free hemoglobin solution;
   (b) adding to the concentrated hemoglobin solution a stabilizing effective amount of at least one member selected from the group consisting of adenine, inosine, and adenosine triphosphate; and glucose; and
   (c) ejecting the hemoglobin solution from an orifice for liposomerization at a temperature below 40° C.

10. The method of claim 9, wherein the concentrated hemoglobin solution of (b) further comprises phosphoenol pyruvic acid.

11. A hemoglobin-encapsulated liposome produced by the method of claim 9.

12. A hemoglobin-encapsulated liposome produced by the method of claim 10.

* * * * *

UNITED STATES PATENT AND TRADEMARK OFFICE
CERTIFICATE OF CORRECTION

PATENT NO. : 5,674,528
DATED : October 7, 1997
INVENTOR(S) : Yoshitaka OGATA et al It is certified that error appears in the above-identified patent and that said Letters Patent is hereby corrected as shown below:

On the title page, insert the below info.

-- [*] Notice: The term of this patent shall not extend beyond the expiration date of Pat. No. 5,688,526 --.

In Column 5, line 34, delete "Glucose" and insert -- glucose --.

Signed and Sealed this

Fourth Day of August, 1998

Attest:

BRUCE LEHMAN

Attesting Officer

Commissioner of Patents and Trademarks